United States Patent [19]

Sidorenko et al.

[11] 4,409,985

[45] Oct. 18, 1983

[54] ELECTRONIC ERGOMETER FOR CARDIAC ARRHYTHMIA PATIENTS

[76] Inventors: Georgy I. Sidorenko, ulitsa Pulikhova, 7, kv. 37; Vladimir I. Stankevich, ulitsa Plekhanova, 32, korpus 2, kv. 84; Vladimir M. Yakubovich, 1 pereulok Opanskogo, 4, kv. 1; Yaroslav G. Nikitin, ulitsa Pritytskogo, 54, kv. 354, all of Minsk, U.S.S.R.

[21] Appl. No.: 247,238

[22] Filed: Mar. 25, 1981

[51] Int. Cl.³ .............................................. A61B 5/02
[52] U.S. Cl. .................................... 128/702; 128/707
[58] Field of Search ................ 128/696, 702, 707, 782

[56] References Cited

U.S. PATENT DOCUMENTS 3,845,756 11/1974 Olsson .............................. 128/707
4,224,952 9/1980 Sidorenko et al. .................. 128/782

FOREIGN PATENT DOCUMENTS

665888 6/1979 U.S.S.R. .............................. 128/707
768391 1/1980 U.S.S.R. .............................. 128/707

Primary Examiner—Kyle L. Howell
Assistant Examiner—Francis J. Jaworski
Attorney, Agent, or Firm—Bruce E. Lilling; Burton L. Lilling; Myron Greenspan

[57] ABSTRACT

An electronic ergometer for cardiac arrhythmia patients is disclosed, and it is capable of determining and indicating the magnitude of power developed by an individual. In addition, it can indicate the power at which a cardiac arrhythmia occurs. In one embodiment of the invention, the electronic ergometer is capable of storing the magnitude of power developed by the patient at which the cardiac arrhythmia occurred. The device consists of various electronic components encased in a simple housing attached to the belt, or other clothing, of the patient. It is used by the patient during physical activity, in order to monitor the work and power of the patient. In addition, since an electrocardiogram sensor is provided, the unit sounds an alarm when a cardiac arrhythmia occurs. This advises the patient to cease his working and to rest.

3 Claims, 4 Drawing Figures

ELECTRONIC ERGOMETER FOR CARDIAC ARRHYTHMIA PATIENTS

FIELD OF THE INVENTION

The present invention relates to devices for registering loads exerted on an individual performing movements, and more particularly to electronic ergometers.

The present invention can be used in medical scientific research, in medical practice, in sports, in curative physical culture exercises, in health resort service, and in space medicine.

BACKGROUND OF THE INVENTION

Cardiovascular disorders come first in the world as far as lethality and invalidization of people are concerned.

In the recent years there has been an awakening to the need for a more systematized approach to the problem of physical exercise. Particularly, individuals in the over-thirty years age bracket are having routine exercise prescribed by their physicians as a preventive measure against heart desease and other associated cardiovascular disorders. Numerous recent publications have recognized a correlation between physical fitness and exercise and have delineated detailed regimens or programs of physical exercise intended to yield the desired results. This physical exercise must be performed only under medical supervision with constant checks on physical loads and the physical activity of the exerciser.

Besides, in the course of medical examination it is often necessary to know about a person's heart activity when the person is subjected to various physical loads.

DESCRIPTION OF THE PRIOR ART

Known in the art is an apparatus for detecting cardiac arrhythmias in a person during rest, under physical load or during transient process (cf. U.S.S.R. Author's Certificate No. 651,785).

This apparatus comprises a clock-pulse generator, a frequency divider having a division ratio of 1:5, two binary counters, a reversible counter, a comparison unit and a control unit.

The control unit, which is supplied with an electrocardiogram (ECG) signal, develops three control signals sychronized with the R-wave of the ECG signal, said control signals being in phase with the pulses produced by the clock-pulse generator.

The frequency divider divides the number of the clock-pulses occurring between the adjacent R-waves. The number of the pulses at the output of the frequency divider is counted by the binary counter. The binary counter produces a dynamic reference value equal to 0,2 of the RR-interval. The dynamic reference value is applied to an input of the comparison unit whose other input is supplied with the value of $\Delta RR$. The latter value is obtained from the reversible counter which, on command from the control unit, is stored from the binary counter with the value of an $RR_i$-interval and, on another command from the control unit, subtracts from this value the value of the $RR_{i+1}$-interval.

The comparison unit compares the value of $\Delta RR = RR_i - RR_{i+1}$ with the dynamic reference value which is equal to 0,2 RR. In case of occurrence of an arrhythmia, the value of $\Delta RR$ will be greater than 0,2 RR and the comparison unit develops a signal indicating the presence of an arrhythmia.

This apparatus, being capable of detecting the presence of an arrhythmia, does not permit estimation of the magnitude of physical load at which an arrhythmia occurs. Such estimation is of great importance to cardiac patients undergoing medical rehabilitation after myocardial infarction because any deviation from normal heart activity may lead in that case to recurrence of infarction.

Also known is an electronic ergometer comprising a serial arrangement of a transducer for converting the oscillations of the body center of gravity of an individual into an electrical signal and constituted by seismic pickup, and a pulse shaper whose output is connected to an adjustable high-frequency multivibrator. The output of the multivibrator is connected to a frequency divider whose output is connected to the counting inputs of a first multi-digit counter and of a second multi-digit counter. The outputs of the first multi-digit counter are connected to the inputs of an indicator. The control input and one of the reset inputs of the second counter are connected to an adjustable timer. The outputs of the second counter are connected to the inputs of a power indication enabling unit whose outputs are connected to the inputs of the indicator. The reset inputs of the frequency divider and of the first counter and another rest input of the second counter are connected to the zero-setting unit. The control inputs of the indicator and of the power indication enabling unit are connected to an indication switching unit (cf. Allowed Application No. 2,635,500/18-10 for U.S.S.R. Author's Certificate, filed Dec. 12, 1978).

Such an ergometer is capable of measuring and registering work performed by the individual and, when the amount of work reaches a predetermined magnitude, of generating audible and visual signals indicating that the reserve is used up. The current magnitude of the performed work and the achievement of the permissible magnitude of work are indicated by a digital indicator built directly into the apparatus. This makes possible constant monitoring of the work performed by the individual and enables the individual to be alerted when the permissible amount of work is used up.

In such an ergometer power is measured by counting the amount of work performed in a time interval determined by the adustable timer. The time interval provided by the timer may be selected over a wide range according to the purpose which should be achieved and may be, for example, 1 sec., 10 sec., 1 min. and so on.

The known ergometer is capable of measuring and registering work performed by the individual and power developed thereby while performing work. However, it does not provide detection of a cardiac arrhythmia when work is being performed. In the course of medical examination it is often necessary to know about the heart activity when the individual is subjected to various physical loads.

In order to judge the heart activity it is desirable to have information on the magnitude of power which causes an arrhythmia when an individual is subjected to physical load.

SUMMARY OF THE INVENTION

Accordingly, it is an object of the present invention to provide an electronic ergometer capable of determining and indicating the magnitude of power developed by an individual, at which a cardiac arrhythmia occurs.

Another object of the present invention is to provide an electronic ergometer capable of storing the magnitude of power developed by an individual, at which a cardiac arrhythmia occurs.

With these and other objects in view there is proposed an electronic ergometer having a housing accomodating a transducer for converting the oscillations of the body center of gravity of an individual into an electrical signal and having its output connected to the input of a pulse shaper; an adjustable high-frequency multivibrator having its control input connected to the output of the pulse shaper; a frequency divider having its counting input connected to the output of the adjustable high-frequency multivibrator; a first counter having its counting input connected to a first output of the frequency divider; an indicator having information inputs connected to the outputs of the first counter; a second counter having its counting input connected to a second output of the frequency divider; an adjustable timer having its output connected to the control and reset inputs of the second counter; a register having its reset input connected to the output of the adjustable timer, its information inputs connected to the outputs of the second counter and its outputs connected to the inputs of a power indication enabling unit whose outputs are connected to information inputs of the indicator; an indication switching unit having its output connected to a first control input of the indicator and to the control input of a power indication enabling unit; a low-frequency multivibrator; and a mixer having one input connected to the output of the adjustable high-frequency multi-vibrator, its other input connected to the output of the low-frequency multivibrator and its output connected to the signal input of the indicator. According to the invention, the invention further comprises an ECG sensing unit; an arrhythmia signal generating means including an arrhythmia sensing unit and a monostable multivibrator connected in series, the input of the arrhythmia sensing unit being connected to the output of the ECG sensing unit; and a unit for enabling indication of power at which an arrhythmia occurs which has its information inputs connected to the outputs of the register and its outputs connected to information inputs of the indicator. The output of the monostable multivibrator is connected to a second control input of the indicator, to the control input of the register, to the control input of the unit for enabling indication of power at which an arrhythmia occurs, and to the input of the low-frequency multivibrator.

Introduction of the arrhythmia and ECG sensing units into the ergometer provides detection of a cardiac arrhythmia when the individual is subjected to physical load.

Introduction of the arrhythmia signal generating means including the arrhythmia sensing means and the monostable multivibrator provides, upon arrival of the signal from the ECG sensing unit, generation of a signal of required length to control the operation of the indicator, of the unit for enabling indication of power at which an arrhythmia occurs and of the register. As long as the signal at the output of the arrhythmia signal generating means exists, the indicator produces visual and audible signals indicating the presence of an arrhythmia.

Introduction of the unit for enabling indication of power at which an arrhythmia occurs allows the information on the magnitude of power whih has caused arrhythmia to be passed to the register and to the indicator upon generation of a signal by the arrhythmia signal generating unit.

According to one embodiment of the invention, the unit for enabling indication of power at which an arrhythmia occurs has an additional control input, and the electronic ergometer further comprising a storage unit having its information inputs connected to the outputs of the register and its outputs connected to information inputs of the unit for enabling indication of power at which an arrhythmia occurs; a distributor having its outputs connected to the address inputs of the storage unit; a reversible counter having its up-counting input connected to the output of the monostable multivibrator and its outputs connected to the inputs of the distributor and to information inputs of the unit for enabling indication of power at which an arrhythmia occurs; an OR circuit having one input connected to the output of the monostable multivibrator and its output connected to the second control input of the indicator; and a read-out unit having its output connected to the additional control input of the unit for enabling indication of power at which an arrhythmia occurs, to another input of the OR circuit and to the down-counting input of the reversible counter.

Introduction of the storage unit into the ergometer provides storage of the magnitude of power which has caused an arrhythmia.

Introduction of the distributor allows information to be written into the corresponding cell of the storage unit, the number of the cell being determined by the distributor output at which a signal is developed.

Introduction of the reversible counter into the ergometer makes it possible to determine the sequence number of an arrhythmia, which sequence number is indicated by the indicator and defines the number of the storage unit cell. Reversible counting permits the cell number to be selected in one order during writing and in the reverse order during reading, which makes the device more convenient in use.

Introduction of the read-out unit allows retrieval from the storage unit of the magnitude of power which has caused an arrhythmia and to indicate on the indicator display the sequence number of an arrhythmia and the magnitude of power at which an arrhythmia occurs.

Introduction of the OR circuit allows the control signal to be supplied to the indicator either directly upon occurrence of an arrhythmia or during reading.

According to another embodiment of the invention, the arrhythmia sensing unit has an additional output and the unit for enabling indication of power at which an arrhythmia occurs has an additional control input, and the electronic ergometer further comprising a storage unit having its information inputs connected to the outputs of the register and its output connected to information inputs of the unit for enabling indication of power at which an arrhythmia occurs; a distributor having its outputs connected to the address inputs of the storage unit; a reversible counter having its up-counting input connected to the additional output of the arrhythmia sensing unit and its outputs connected to the inputs of the distributor and to information inputs of the unit for enabling indication of power at which an arrhythmia occurs; an OR circuit having one input connected to the output of the monostable multivibrator and its output connected to the second control input of the indicator; and a read-out unit having its output connected to the additional control input of the unit for enabling indication of power at which an arrhythmia occurs, to another input of the OR circuit and to the down-counting input of the reversible counter.

With the arrhythmia sensing unit provided with an additional output connected to the up-counting input of the reversible counter, it is possible to detect a dangerous kind of arrhythmia and to warn the individual about the occurrence of such an arrhythmia.

Over a hundred different kinds of arrhythmia are known, of which 45 are most commonly found. Some of these kinds are most dangerous. For example, an atrio-ventricular block leads to appearance of a sino-auricular block unless the physical load exerted on the individual is removed. A sino-auricular block leads, in turn, to an asystolia (to cardiac arrest and clinical death). An asystolia is a probable outcome when a dangerous kind of arrhythmia occurs unless the load is removed. A still more probable outcome, however, is fibrillation (fibrilary heart contractions, clinical death) which is caused by a paroxismal ventricular tachiocardia which, in turn, is caused by a ventricular extrasystole representing the most common kind of arrhythmia.

On the hand, single extrasystoles are not dangerous even to an individual undergoing physical strain. Likewise, there is no danger in some other kinds of arrhythmia. Therefore it is necessary to discriminate between the dangerous kinds of arrhythmia and the kinds that are not dangerous.

The proposed electronic ergometer alerts the individual to the recurrence of any kind of arrhythmia and indicates the magnitude of physical load at which an arrhythmia occurs. This is expedient during medical examination and in some other cases, but in everyday life or during work or athletic training there is no need to know about the occurrence of all kinds of arrhythmia; it is sufficient to alert the individual to the occurrence of the dangerous kinds and to indicate the physical load which has caused an arrhythmia. Indication (audible and visual) in these cases informs the individual about the need for removal of the load and thus prevents the appearance of an asystolia or cardiac fibrillation.

BRIEF DESCRIPTION OF THE DRAWINGS

The aforementioned and other objects and advantages of the present invention will become more apparent upon consideration of the following detailed description of its preferred embodiments taken in conjunction with the accompanying drawings.

DETAILED DESCRIPTION OF THE INVENTION

The proposed electronic ergometer 1 (FIG. 1) enclosed in a housing 2 is positioned on the waistband of an individual, i.e., of a subject 3 to be studied. An ECG sensing unit 4 is attached to the heart region of the chest of the individual. The oscillations of the body center of gravity of the individual act on a transducer 5 (FIG. 2) which includes a seismic pickup (not shown) and converts the oscillations of the body center of gravity of the individual into an electrical signal. The output of the seismic pickup of the transducer 5 is connected to a pulse shaper 6. The pulse shaper 6 may be a threshold circuit. The output of the pulse shaper 6 is connected to the control input of an adjustable high-frequency multivibrator 7.

Figure 2:
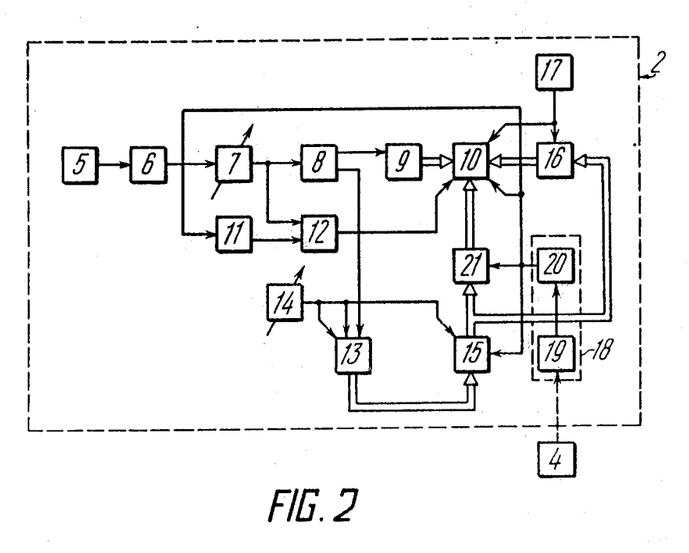
FIG. 2 is a block-diagram of an electronic ergometer, according to the invention.

The output of the multivibrator 7 is connected to the counting input of a frequency divider 8 which is a multi-digit binary counter. The frequency divider 8 has two outputs, a first output of the frequency divider 8 being connected to the counting input of a counter 9 which is a multi-digit binary counter. The counter 9 has a plurality of outputs equal in number to the number of bit positions of the counter 9. The outputs of the counter 9 are connected to information inputs of an indicator 10.

A low-frequency multivibrator 11 is connected to one of the inuts of a mixer 12, which is an AND circuit, a second input of the mixer 12 being connected to the output of the multivibrator 7, while the output of the mixer 12 is connected to the signal input of the indicator 10.

A second output of the frequency divider 8 is connected to the counting input of a counter 13 which is a multi-digit binary counter. The control and reset inputs of the counter 13 are connected to the output of an adjustable timer 14. The outputs of the counter 13 are equal in number to the number of bit positions of the counter 13 and are connected to corresponding information inputs of a register 15 whose outputs are connected to a power indication enabling unit 16. The reset input of the register 15 is connected to the output of the timer 14.

The power indication enabling unit 16 consists of a plurality of AND circuits (not shown) equal in number to the number of outputs of the register 15. One of the inputs of each of the AND circuits is connected to a corresponding output of the register 15, the other input of each of the AND circuits being connected to the output of an indication switching unit 17 and to a first control input of the indicator 10. The outputs of the AND circuits represent the outputs of the power indication enabling unit and are connected to corresponding information inputs of the indicator 10.

The indication switching unit 17 is a threshold circuit controlled by a push-button (not shown). The duration of the signal at the output of the power indication switching unit 16 equals the time period during which the push-button remains pressed and determines the time period during which the magnitude of power is indicated on the display of the indicator 10.

The ergometer further comprises an arrhythmia signal generating means 18 including an arrhythmia sensing unit 19 and a monostable multivibrator 20 connected in series, the input of the arrhythmia sensing unit 19 being connected to the output of the ECG sensing unit 4. The output of the monostable multivibrator 20 is connected to the control input of the register 15, to the control input of a unit 21 for enabling indication of power at which an arrhythmia occurs, to a second control input of the indicator 10 and to the input of the low-frequency multivibrator 11.

The outputs of the register 15 are connected to corresponding information inputs of the unit 21 for enabling indication of power at which an arrhythmia occurs. The unit 21 consists of a plurality of AND circuits (not shown) equal in number to the number of outputs of the register 15. One of the inputs of each of the AND circuits is connected to a corresponding output of the register 15, the other input of each of the AND circuits being connected to the output of the monostable multivibrator 20, to a second control input of the indicator 10 and to the control input of the register 15. The outputs of the AND circuits represent the outputs of the unit 21 and are connected to corresponding information inputs of the indicator 10.

The electronic ergometer is supplied from an independent power supply unit (not shown).

Figure 3:
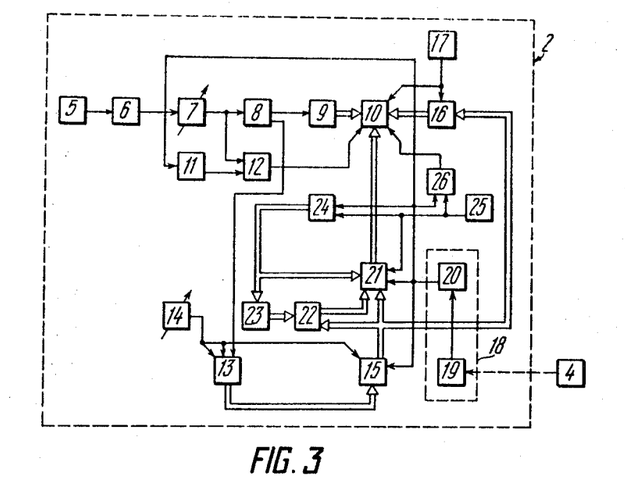
FIG. 3 is a block-diagram of an electronic ergometer, according to one of the embodiments of the invention.

FIG. 3 shows another embodiment of the electronic ergometer 1 (FIG. 1) wherein the unit 21 (FIG. 3) for enabling indication of power at which an arrhythmia occurs is provided with an additional control input. Besides, the electronic ergometer further comprises a storage unit 22 having its information inputs connected to corresponding outputs of the register 15 and its outputs connected to corresponding information inputs of the unit 21. The address inputs of the storage unit 22 are connected to the outputs of a distributor 23 which is a binary decoder. The inputs of the distributor 23 are connected to corresponding outputs of a reversible counter 24.

The additional control input of the unit 21 for enabling indication of power at which an arrhythmia occurs and the down-counting input of the reversible counter 24 are connected to the output of a read-out unit 25.

The output of the monostable multivibrator 20 is connected to the up-counting input of the reversible counter 24 and to one input of an OR circuit 26, the other input of the OR circuit 26 being connected to the output of the read-out unit 25. The output of the OR circuit 26 is connected to the second control input of the indicator 10.

Figure 4:
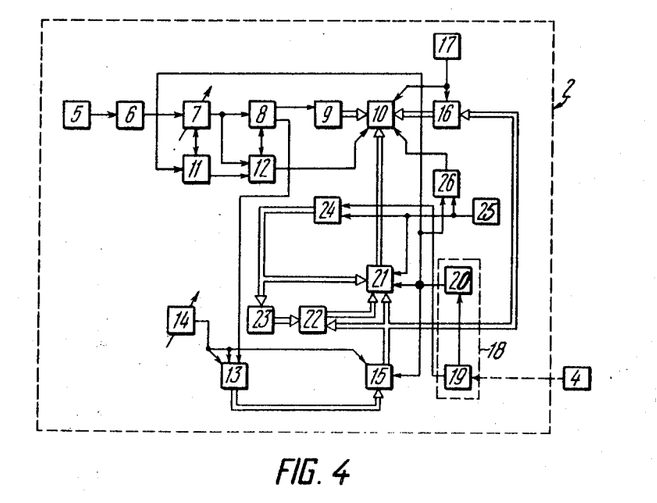
FIG. 4 is a block-diagram of an electronic ergometer, according to another embodiment of the invention.

FIG. 4 shows still another embodiment of the electronic argometer 1 (FIG. 1) wherein the arrhythmia sensing unit 19 (FIG. 4) is provided with another output constituting the second output of the arrhythmia sensing unit 19 and connected to the up-counting input of the counter 24.

The electronic ergometer 1 (FIG. 1) operates as follows.

Figure 1:
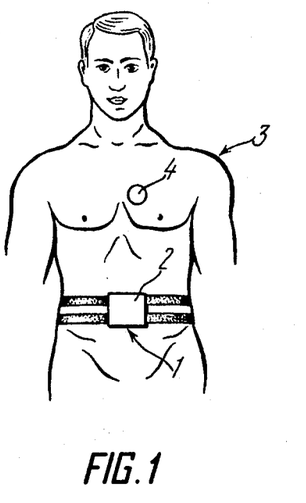
FIG. 1 shows how the proposed electronic ergometer with an ECG sensing unit is arranged on a person to be studied, according to the invention.

The housing 2 of the electronic ergometer 1 is placed on the waistband of the individual—of the subject 3 to be studied.

The frequency of the adjustable high-frequency multivibrator 7 (FIG. 2) is set according to the specific characteristics of the individual. The time period over which the magnitude of power shall be estimated is selected by setting the time intervals produced by the adjustable timer 14. The ECG sensing unit 4 is attached to the heart region of the body of the individual.

The power supply unit is switched on, whereupon the frequency divider 8, the counters 9 and 13 and the register 15 are automatically set to zero and the ergometer is ready for operation.

The operation of the ergometer is based on conversion of the oscillations of the body center of gravity of the individual into an electrical signal, the duration of which is proportional to the amplitude of these oscillations.

During walking, running or jogging the body center of gravity of the individual performs oscillatory motions converted by the transducer 5 into an electrical signal, the duration of which is proportional to the amplitude of oscillations of the body center of gravity. The signal from the output of the transducer 5 is applied to the input of the pulse shaper 6 which eliminates "rattle" in the edges of the signal produced by the transducer 5. The signal developed by the pulse shaper 6 is applied to the control input of the adjustable high-frequency multivibrator 7 which, upon application of the signal from the pulse shaper 6, generates pulses having a high repetition rate. Thus the multivibrator 7 develops at its output pulse trains equal in number to the number of oscillations of the body center of gravity of the individual, the number of pulses in a train depending on the amplitude of oscillations of the body center of gravity and on the specific characteristics of the individual (weight, height), i.e. on the frequency of the high-frequency multivibrator 7.

The signal from the high-frequency multivibrator 7 is applied to the frequency divider 8 constituted by a two-digit counter having two outputs (corresponding to bit positions of the counter). The pulses appearing at the output of the frequency divider 8 connected to the input of the counter 13 are equivalent of one unit of work, while the pulses appearing at the other output are equivalent of 100 work units. The signal from the second output of the frequency divider 8 (100 work units) is applied to the counting input of the counter 9 which develops at its outputs a binary code corresponding to the amount of work performed by the individual. This code is applied to information inputs of the indicator 10 and is indicated on its display in the form of arabic numerals of the decimal number system, with the value of the lowest order digit equal to 100 work units.

The signal equivalent of one work unit is applied to the counting input of the counter 13 which, during the time interval determined by the adjustable timer 14, counts the magnitude of power developed by the individual. The binary code from the outputs of the counter 13 is applied to the information inputs of the register 15 wherein it remains stored until the end of the time interval set by the timer 14.

Upon termination of said time interval the register 15 is set to zero by a signal applied to its reset input. Thereupon the register 15 is stored with a new magnitude of power from the counter 13.

Thus the register 15 retains the magnitude of power obtained during the last occuring period of measurement.

The register 15 is connected to the information inputs of the power indication enabling unit 16 which, in response to the signal from the indication switching unit 17, passes information from the output of the register 15 to information inputs of the indicator 10. The latter, in response to the signal from the indication switching unit 17, stops indicating the magnitude of work and starts indicating the magnitude of power. The signal at the output of the indication switching unit 17 appears at the instant the push-button of the indication switching unit is pressed.

Therefore the indicator 10 displays the magnitude of work or power according to the value of the control signal at the first control input of the indicator 10.

Simultaneously with work and power measurements, the ergometer monitors the individual's heart activity by means of the arrhythmia signal generating means 18.

It is possible that the power developed by the individual will cause a cardiac arrhythmia. This power may prove to be less than the permissible power threshold due to general fatigue of the individual (e.g., a large amount of work has been performed before). But the fact of appearance of an arrhythmia is in itself enough to necessitate load removal.

The presence of an arrhythmia causes the arrhythmia sensing unit 19 to produce a signal at its output. This signal is applied to the input of the monostable multivibrator 20 which is a one-shot circuit generating a pulse of considerable length, e.g. having a duration of 30 sec.

As long as this pulse exists at the output of the multivibrator 20, the register 15 cannot be reset (the control input of the register 15 is supplied with a signal which inhibits resetting). The same pulse is applied to the control input of the unit 21 for enabling indication of power at which an arrhythmia occurs, to the second control input of the indicator 10 and to the input of the low-frequency multivibrator 11. In response to this signal the unit 21 passes information from the register 15 to the indicator 10 which, in response to the control signal applied to the second control input, stops indicating work and indicates the magnitude of power stored in the register 15. Since the register 15 is stored with the magnitude of power measured during the previous measurement period and the transient time of the human organism is 10 to 15 sec. (i.e., is commensurable with the time period required for power measurement which is 10 sec.), the indicator 10 indicates the magnitude of power at which the arrhythmia occurred.

The signal from the monostable multivibrator 20 turns on the low-frequency multivibrator 11. The mixer 12 mixes the frequencies of the multivibrators 7 and 11 and supplies pulse trains to the signal input of the indicator 10. In response to application of pulses to its signal input the indicator 10 produces an intermittent audible signal and its display begins to blink. The development of the audible and visual signals indicates the presence of an arrhythmia and warns the individual about the necessity of ceasing movements. Upon termination of the signal at the output of the multivibrator 20 the ergometer stops generating the audible signal and indicating the magnitude of power at which the arrhythmia occurred.

If the electronic ergometer 1 (FIG. 1) is made as shown in FIG. 3, it operates as follows.

The work and power measurements are carried out as described above. In case of occurrence of an arrhythmia the control input of the register 15, the first control input of the unit 21 for enabling indication of power at which an arrhythmia occurs and, via the OR circuit 26, the control input of the indicator 10 are supplied with a pulse from the monostable multivibrator 20. Then the presence of the arrhythmia, as well as the magnitude of power which caused the arrhythmia, is indicated in the same way as described above. Simultaneously the pulse from the output of the monostable multivibrator 20 is applied to the up-counting input of the reversible counter 24, as a result of which the counter 24 develops at its outputs a binary code corresponding to the sequence number of the arrhythmia pulse.

The binary code from the outputs of the reversible counter 24 is applied to the inputs of the distributor 23 and to information inputs of the unit 21 for enabling indication of power at which an arrhythmia occurs. From the output of the unit 21 the binary code passes to the indicator 10 and is indicated on its display as a sequence number.

The application of the binary code from the outputs of the reversible counter 24 to the inputs of the distributor 23 leads to appearance of a signal at one of the outputs of the latter (according to the code supplied from the counter 24), which output determines the number of the cell of the storage unit 22 into which the magnitude of power stored in the register 15 is written. When a new arrhythmia occurs, the code at the outputs of the counter 24 changes bringing about a corresponding change in the cell number.

Thus, each occurrence of an arrhythmia causes the indicator 10 to produce an audible and a visual signal and to indicate on the display the magnitude of power at which the arrhythmia occurred, as well as the sequence number of the arrhythmia. In addition, the magnitudes of power which has caused arrhythmias are stored into the corresponding cells of the storage unit 22.

Upon termination of the pulse produced by the monostable multivibrator 20, the indicator 10 stops generating the audible signal and indicating the power at which the arrhythmia occurred.

On hearing the audible signal the individual must cease moving and can read from the digital display of the indicator 10 the magnitude of power which has caused an arrhythmia.

After having a rest for a time period prescribed by a physician the individual may resume movements.

After the end of the studies it is necessary to read out the magnitude of power which has caused an arrhythmia (if it occurred during movements).

This is achieved by pressing the push-button (not shown) of the read-out unit 25 whereby a signal is supplied to the down-counting input of the reversible counter 24 and to the second control input of the unit 21 for enabling indication of power at which an arrhythmia occurs. The indicator 10 indicates on its digital display the sequence number of an arrhythmia and the magnitude of power which has caused this arrhythmia.

As the push-button is repeatedly pressed, the information stored in the cells of the storage unit 22 is retrieved in the reverse order, so that each time the push-button is pressed the indicator 10 displays a new sequence number of arrhythmia (which is less by one than the previous number) and the corresponding magnitude of power.

If necessary, all these magnitudes of power can be taken down. The push-button of the read-out unit is repeatedly pressed until the reversible counter 24 is set to zero, i.e. until all the magnitudes of power which have cause arrhythmias are retrieved from the storage unit 22.

If the electronic ergometer 1 (FIG. 1) is made as shown in FIG. 4, it operates as follows.

Simultaneously with the measurement of work performed by the individual and of power developed thereby, the ergometer, with the aid of the arrhythmia sensing unit 19, which may be, for example, an arrhythmia detector, monitors the individual's heart activity while work is being performed.

It may happen that the power developed by the individual will cause a cardiac arrhythmia and yet this power will be below the permissible power threshold because of general fatigue of the individual (e.g., a large amount of work has been performed before).

Upon appearance of a kind of arrhythmia which is not dangerous, a signal from the second output of the arrhythmia sensing unit 19 is applied to the up-counting input of the reversible counter 24 which develops at its outputs a binary code supplied to the inputs of the distributor 23 and to information inputs of the unit 21 for enabling indication of power at which an arrhythmia occurs. The distributor 23 develops a signal at one of its outputs according to the binary code supplied to its inputs. The output signal of the distributor 23 determines the number of the cell of the storage unit 22 into which the magnitude of power stored in the register 15 is written.

Upon application of a new signal from the second output of the arrhythmia sensing unit 19 to the up-counting input of the reversible counter 24 the magnitude of power retained in the register 15 at that instant is written into the storage unit cell having the next number.

After the end of the studies and, if necessary, in other cases information from the storage unit 22 is read out with the aid of the read-out unit 25. This is accomplished by pressing the push-button of the read-out unit 25 whereby a signal is supplied to the down-counting input of the reversible counter 24. The signal from the read-out unit 25 is also applied to the second control input of the unit 21 for enabling indication of power at which an arrhythmia occurs and to the second input of the OR circuit 26.

In response to this signal the distributor 23 selects the cell in the storage unit 22 and the unit 21 passes the magnitude of power which has caused an arrhythmia, as well as the sequence number of this arrhythmia, to the indicator 10 which, upon application of the signal from the OR circuit 26, will indicate on the digital display the magnitude of power which has caused the arrhythmia and the sequence number of this arrhythmia.

Each subsequent pressing of the push-button of the read-out unit 25 leads to appearance of a new sequence number of arrhythmia and of a new magnitude of power on the indicator display.

The push-button of the read-out unit 25 is repeatedly pressed until the counter 24 is set to zero, i.e. until all the magnitudes of power which have caused arrhythmias are retrieved from the storage unit 22.

Upon appearance of a dangerous kind of arrhythmia the arrhythmia sensing unit 19 develops at its first output a signal applied to the input of the monostable multivibrator 20. The output signal of the multivibrator 20 is applied to the input of the low-frequency multivibrator 11.

In this case one of the inputs of the mixer 12 is supplied with the pulses from the output of the high-frequency multivibrator 7, while the other input of the mixer 12 is supplied with the pulses from the output of the low-frequency multivibrator 11. The mixer 12 mixes the frequencies of the multivibrators 7 and 11 and supplies pulse trains to the signal input of the indicator 10, as a result of which the latter starts generating an intermittent audible signal and its display begins to blink.

Simultaneously with the application of a signal to the input of the low-frequency multivibrator 11 from the output of the multivibrator 20, the signal from the output of the multivibrator 20 is applied to the control input of the unit 21 for enabling indication of power at which an arrhythmia occurs, to the control input of the register 15 and to the first input of the OR circuit 26.

In response to this signal the unit 21 transfers data from the register 15 to the indicator 10 and the latter, upon arrival of the signal from the output of the OR circuit 26, indicates the magnitude of power which has caused an arrhythmia.

As soon as the ergometer generates a signal indicating the presence of a dangerous kind of arrhythmia, the individual should cease moving (performing physical exercise) and then memorize or take down the magnitude of power.

When the power supply is cut off the ergometer loses all the information.

Therefore, the ergometer, being capable of measuring work and power, also permits determination of that magnitude of power developed by an individual subjected to physical load, which causes an arrhythmia. Upon appearance of any kind of arrhythmia the ergometer generates a warning signal in response to which the individual must cease performing movements. One version of the ergometer is capable of storing the magnitude of power which has caused an arrhythmia. Another embodiment is capable of discriminating between physical loads according to the kinds of arrhythmia caused thereby. Thus, if the occurring kinds of arrhythmia is not dangerous, the ergometer does not indicate the magnitude of power and generates no warning signal but stores the power magnitude into the storage unit so that the magnitude of power which has caused an arrhythmia can be determined. If a dangerous kind of arrhythmia occurs, the ergometer generates a warning signal in response to which the individual must immediately cease performing movements.

The employment of the electronic ergometer permits cardiac patients to extend the range of their movements during medical rehabilitation without increasing the risk of recurrence of infarction.

The electronic ergometer is made as a portable device and can be carried on the person of the subject to be studied.

While the invention is described herein in the terms of the preferred embodiments, numerous modifications may be made without departure from the spirit and scope of the invention as defined in the appended claims.

We claim:

1. An electronic ergometer for measuring work performed by an individual and power developed thereby while performing work at which a cardiac arrhythmia occurs by measuring the oscillations of the body center of gravity of the individual, comprising:

a transducer means for converting the oscillations of the body center of gravity of said individual into an electrical signal provided as an output, said transducer being implemented as at least one seismic pickup having an output;

a pulse shaper including a threshold element having an input and an output, said input being connected to said output of said transducer;

an adjustable high-frequency multivibrator having a control input and an output of settable frequency, said control input being connected to said output of said pulse shaper;

a frequency divider having a counting input, a first output and a second output, said counting input being connected to said output of said adjustable high-frequency multivibrator;

a first counter having a counting input and a plurality of bit position outputs equal in number to the number of bit positions of the counter, said counting input being connected to said first output of said frequency divider; an indicator having a first control input, a second control input, a signal input, a first plurality of information inputs and a second plurality of information inputs, the inputs of said first plurality of information inputs being respectively connected to corresponding bit position outputs of said first counter;

a second counter having a counting input, a reset input, a control input and a plurality of bit position outputs equal in number to the number of bit positions of the counter, said counting input being connected to said second output of said frequency divider;

an adjustable timer having an output, said output being connected to said reset input and to said control input of said second counter;

a register having a control input, a reset input, a plurality of information inputs equal in number to the number of outputs of said plurality of outputs of said second counter, and a plurality of outputs equal in number to the number of bit positions of the register, said reset input being connected to said output of said adjustable timer and corresponding information inputs of said plurality of inputs being respectively connected to corresponding bit position outputs of said second counter;

a power indication enabling unit having a control input, a plurality of inputs equal in number to the number of bit positions of said second counter and a plurality of outputs equal in number to the number of inputs of said plurality of inputs of the unit, corresponding inputs of said plurality of inputs being respectively connected to corresponding bit position outputs of said register and corresponding outputs of said plurality of outputs being respectively connected to corresponding inputs of said second plurality of information inputs of said indicator;

an indication switching unit having an output, said output being connected to said first control input of said indicator and to said control input of said power indication enabling unit;

an ECG sensing unit having an output;

an arrhythmia signal generating means including:

an arrhythmia sensing unit having an input and an output, said input being connected to said output of said ECG sensing unit, and a monostable multivibrator having an input and an output, said input being connected to said output of said arrhythmia sensing unit and said output being connected to said control input of said register and to said second control input of said indicator;

a low-frequency multivibrator having an input and an output, said input being connected to said output of said monostable multivibrator;

a mixer having a first input, a second input and an output, said first input being connected to said output of said adjustable high-frequency multivibrator, said second input being connected to said output of said low-frequency multivibrator and said output being connected to said signal input of said indicator;

a unit for enabling indication of power at which an arrhythmia occurs having a control input, a plurality of information inputs equal in number to the number of outputs of said plurality of outputs of said register, and a plurality of information inputs equal in number to the number of said information inputs, said control input being connected to said output of said monostable multivibrator, corresponding information inputs of said plurality of inputs being respectively connected to corresponding outputs of said register, and corresponding information outputs of said plurality of outputs being respectively connected to corresponding inputs of said first plurality of information inputs of said indicator; and a housing to accomodate said transducer means, said pulse shaper, said adjustable high-frequency multivibrator, said frequency divider, said first counter, said indicator said second counter, said adjustable timer, said power indication enabling unit, said indication switching unit, said arrhythmia signal generating means, said low-frequency multivibrator, said mixer, said register, and said unit for enabling indication of power at which an arrhythmia occurs.

2. An electronic ergometer according to claim 1, wherein said unit for enabling indication of power at which an arrhythmia occurs has a second control input, and said ergometer further comprises:

a storage unit having a plurality of information inputs equal in number to the number of outputs of said plurality of outputs of said register, a plurality of address inputs equal in number to the number of cells of the storage unit, and a plurality of outputs equal in number to the number of inputs of said plurality of information inputs, corresponding inputs of said plurality of information inputs being respectively connected to corresponding outputs of said register and corresponding outputs of said plurality of outputs being respectively connected to corresponding inputs of said plurality of information inputs of said unit for enabling indication of power at which an arrhythmia occurs;

a reversible counter having an up-counting input, a down-counting input and a plurality of outputs equal in number to the number of bit positions of the counter, said up-counting input being connected to said output of said monostable multivibrator, corresponding outputs of said plurality of outputs being respectively connected to corresponding inputs of said plurality of information inputs of said unit for enabling indication of power at which an arrhythmia occurs;

a distributor having a plurality of inputs equal in number to the number of outputs of said plurality of outputs of said reversible counter, and a plurality of outputs equal in number to the number of cells of said storage unit, corresponding inputs of said plurality of inputs being respectively connected to corresponding outputs of said plurality of outputs of said reversible counter, and corresponding outputs of said plurality of outputs being respectively connected to corresponding inputs of said plurality of address inputs of said storage unit;

an OR circuit having a first input, a second input and an output, said first input being connected to said output of said monostable multivibrator and said output being connected to said second control input of said indicator; and a read-out unit having an output, said output being c connected to said second input of said OR circuit, to said down-counting input of said reversible counter and to said second control input of said unit for enabling indication of power at which an arrhythmia occurs.

3. An electronic ergometer according to claim 1, wherein said unit for enabling indication of power at which an arrhythmia occurs has a second control input and said arrhythmia sensing unit has a second output, and said ergometer further comprises:

a storage unit having a plurality of information inputs equal in number to the number of outputs of said plurality of outputs of said register, a plurality of address inputs equal in number to the number of cells of the storage unit, and a plurality of outputs equal in number to the number of inputs of said plurality of information inputs, corresponding information inputs of said plurality of information inputs being respectively connected to corresponding outputs of said register, and corresponding outputs of said plurality of outputs being respectively connected to corresponding inputs of said plurality of information inputs of said unit for enabling indication of power at which an arrhythmia occurs;

a reversible counter having an up-counting input, a down-counting input and a plurality of outputs equal in number to the number of bit positions of the counter, said up-counting input being connected to said second output of said arrhythmia sensing unit and corresponding outputs of said plurality of outputs being respectively connected to corresponding inputs of said plurality of information inputs of said unit for enabling indication of power at which an arrhythmia occurs;

a distributor having a plurality of inputs equal in number to the number of outputs of said reversible counter and a plurality of outputs equal in number to the number of cells of said storage unit, corresponding inputs of said plurality of inputs being respectively connected to corresponding outputs of said plurality of outputs of said reversible counter, and corresponding outputs of said plurality of outputs being respectively connected to corresponding inputs of said plurality of address inputs of said storage unit;

an OR circuit having a first input, a second input and an output, said first input being connected to said output of said monostable multivibrator and said output being connected to said second control input of said indicator; and a read-out unit having an output, said output being connected to said second input of said OR circuit, to said down-counting input of said reversible counter and to said second control input of said unit for enabling indication of power at which an arrhythmia occurs.

* * * * *